(12) United States Patent
Lightner

(10) Patent No.: US 6,432,276 B1
(45) Date of Patent: Aug. 13, 2002

(54) METHOD TO SEPARATE ETHANOL FROM A SOLUTION CONTAINING SULFURIC ACID AND ETHANOL

(76) Inventor: Gene E Lightner, 706 SW. 296th St., Federal Way, WA (US) 98023

( * ) Notice: Subject to any disclaimer, the term of this patent is extended or adjusted under 35 U.S.C. 154(b) by 0 days.

(21) Appl. No.: 09/548,262

(22) Filed: Apr. 12, 2000

(51) Int. Cl.[7] .......................... B01D 3/34; C01B 17/90; C07C 27/28

(52) U.S. Cl. .............. 203/49; 95/258; 127/40; 159/DIG. 19; 203/DIG. 8; 423/525; 568/913

(58) Field of Search .......................... 203/49, 100, 86, 203/21, DIG. 8; 95/141, 258, 253, 39, 46, 60; 568/913; 423/525, 531; 127/40; 159/24.1, 47.1, DIG. 19

(56) References Cited

U.S. PATENT DOCUMENTS

| | | | | |
|---|---|---|---|---|
| 4,608,245 A | * | 8/1986 | Gaddy et al. | 423/531 |
| 4,968,787 A | * | 11/1990 | Inada et al. | 536/18.5 |
| 5,256,173 A | * | 10/1993 | Rastelli | 568/917 |
| 6,007,636 A | * | 12/1999 | Lightner | 127/37 |

* cited by examiner

Primary Examiner—Virginia Manoharan

(57) ABSTRACT

A method to separate ethanol from a solution containing sulfuric acid and ethanol which employs a vessel in which ethanol is humidified from a gas. By adding a gas to a solution containing sulfuric acid and ethanol in the vessel a gas is utilized to form humidified ethanol. Heat is provided to the solution to replace heat of vaporization of the humidified ethanol to maintain a substantially constant thermal equilibrium condition within the vessel to compensate for the energy of ethanol evaporation. The gas humidified with ethanol is then parted from the vessel to remove ethanol from the solution. The sulfuric acid, substantially devoid of ethanol, is likewise removed from the vessel. The ethanol humidified gas is thereupon separated from the ethanol to provide ethanol and a gas containing ethanol. The gas, containing ethanol, is retrieved for recycle to humidify additional ethanol

11 Claims, 2 Drawing Sheets

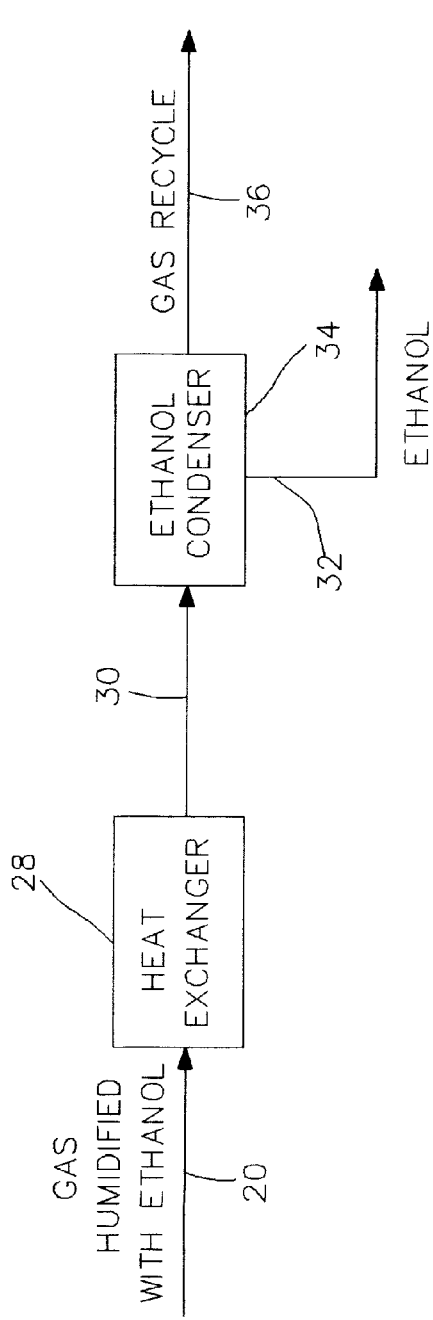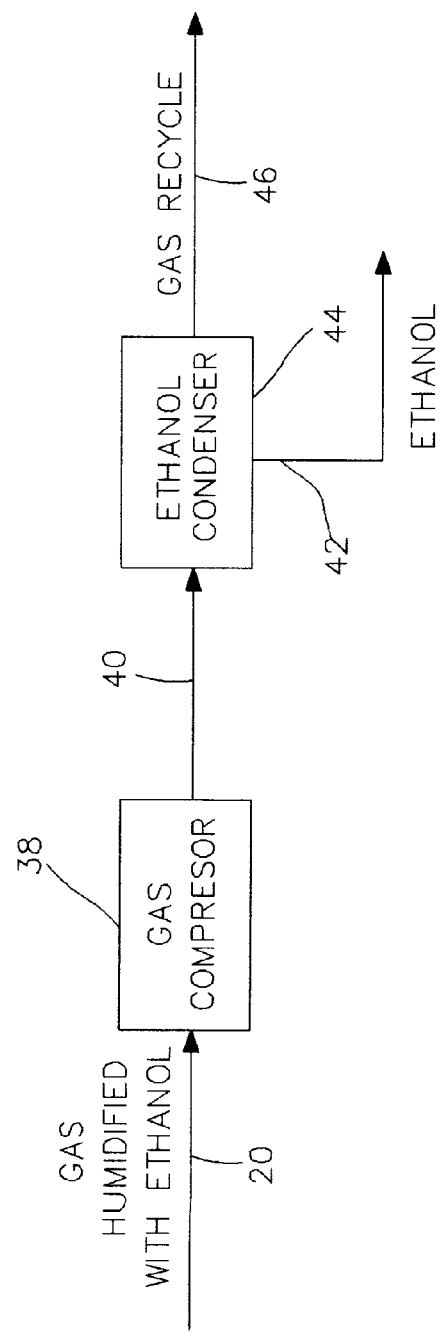

METHOD TO SEPARATE ETHANOL FROM A SOLUTION CONTAINING SULFURIC ACID AND ETHANOL

BACKGROUND OF THE INVENTION

Throughout the world there is increasing interest in converting renewable biomass to usable products such as ethanol. Conversion of wood to ethanol has been practiced during wartime due to a shortage of liquid fuels. Reported in Ind. & Eng. Chem. Vol. 38 No. 9, P. 890 (1946). Because of poor yields and consumption of chemicals the conversion was found not to be economical for peacetime use. Present day interest in hydrolysis of biomass is to provide an alternative fuel source to avoid dependence on unreliable imported petroleum crude oil for liquid fuels. Biomass often contains hemicellulose and lignins accompanying the cellulose contained in the biomass. Hydrolysis of biomass is employed to produce glucose and pentoses. Biomass is a term used to describe material containing cellulose including: paper, pulp, wood waste, sawdust, municipal solid waste (MSW), agricultural wastes, fabrics, and cotton.

A state of the art hydrolysis process, described in U.S. Pat. No. 6,007,636, uses a concentrated acidic liquor to liquefy the carbohydrates in the biomass. A solvent is then employed to form a precipitate of the liquefied carbohydrates in the biomass. The resulting solids are then filtered to separate the solids from the solution of the concentrated acidic liquor and solvent. The resulting filtrate containing concentrated acidic liquor and solvent is then subjected to a separation of the solvent and recycle of the acidic liquor and recovery of solvent is achieved.

Also, a state of the art process being developed by workers at the University of Arkansas, is described in U.S. Pat. No. 4,608,245 and in FY 1997 BIOCHEMICAL conversion/ALCOHOL FUELS PROGRAM: Annual Report page A-85. It employs high concentration of sulfuric acid to convert corn stover to sugars. They describe a process scheme to separate sugars contained in the concentrated sulfuric acid using a heavy boiling solvent to dissolve the sulfuric acid and a low boiling solvent to dissolve the heavy boiling solvent. They also report that this method has a loss of solvents and a loss of sulfuric acid which is neutralized with lime.

Reported in the above named report, on page A-15, is a plan by TVA to develop a high concentration of sulfuric acid process. The current focus of TVA is to develop an inexpensive process for recovering the high concentration of sulfuric acid. Thus the problem of recovering sulfuric acid has not yet been solved.

Recovery of the sulfuric acid is reported as an unsolved problem. Thus it is believed that no satisfactory recovery method has yet been developed.

The present concern is about recovering concentrated sulfuric acid from a solution containing ethanol. This invention relates to a method of recycling concentrated sulfuric acid used to produce depolymerized cellulose and hemicellulose contained in a biomass.

Therefore an object of this invention is to obviate many of the limitations and disadvantages of the prior art to separate solvents from a solution containing sulfuric acid.

Another object of this invention is to avoid use of high boiling solvents to recover sulfuric acid.

Still another object of this invention is to remove ethanol from a solution containing sulfuric acid and ethanol.

Yet another object of this invention is to separate concentrated sulfuric acid from ethanol to produce concentrated sulfuric acid for recycling to produce depolymerized cellulose and hemicellulose contained in a biomass.

In addition, another object of this invention is to separate ethanol from a gas humidified by ethanol.

A further object of this invention is to provide recycling of a gas used to remove ethanol from a solution containing sulfuric acid and ethanol.

Additionally, another object of this invention is to utilize low temperature waste energy to maintain a substantially constant thermal equilibrium condition within the vessel to compensate for the energy of ethanol evaporation.

With the above and other objects in view, this invention relates to the novel features and alternatives and combinations presently described in the brief description of the invention.

BRIEF DESCRIPTION OF THE INVENTION

The present invention, in its broadest aspect, will remove ethanol from a solution containing sulfuric acid and ethanol. By providing a vessel in which ethanol is humidified, and supplying a solution containing ethanol and sulfuric acid, and supplying a gas to humidify the ethanol, the necessary components of the method are hence furnished. The method proceeds by adding the solution to the vessel and combining the gas to form a gas humidified with ethanol, and parting the gas humidified with ethanol from the vessel, and supplying heat to the solution to replace heat of vaporization of the humidified ethanol. The ethanol humidified gas will consequently remove the ethanol from the vessel. The ethanol humidified gas is then separated from the gas to provide ethanol and a gas for recycle to the vessel for use to additionally humidify ethanol. Concentrated sulfuric acid, substantially free of ethanol, is removed from the vessel. In this invention separated concentrated sulfuric acid, from ethanol, is subject to recycle for employment in liquefying cellulose, located in a biomass, followed by hydrolyzing liquefied cellulose in place to form depolymerized cellulose in sulfuric acid. One objective of this invention is to utilize low temperature waste energy to maintain a substantially constant thermal equilibrium condition within the vessel to compensate for the energy of ethanol evaporation.

A method to separate ethanol from a gas is by cooling the humidified gas to substantially condense the ethanol as a liquid and to furnish a gas for recycle.

An alternate method to separate ethanol from a gas is by pressurizing the humidified gas to form a condensation of the ethanol as a liquid and to supply a gas for recycle.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

FIG. 2 is a flow sheet denoting a preferred method for separating ethanol from a gas humidified with ethanol.

FIG. 3 is a flow sheet denoting an alternate method for separating ethanol from a gas humidified with ethanol.

DETAILED DESCRIPTION OF THE PREFERRED EMBODIMENT

Figure 1:
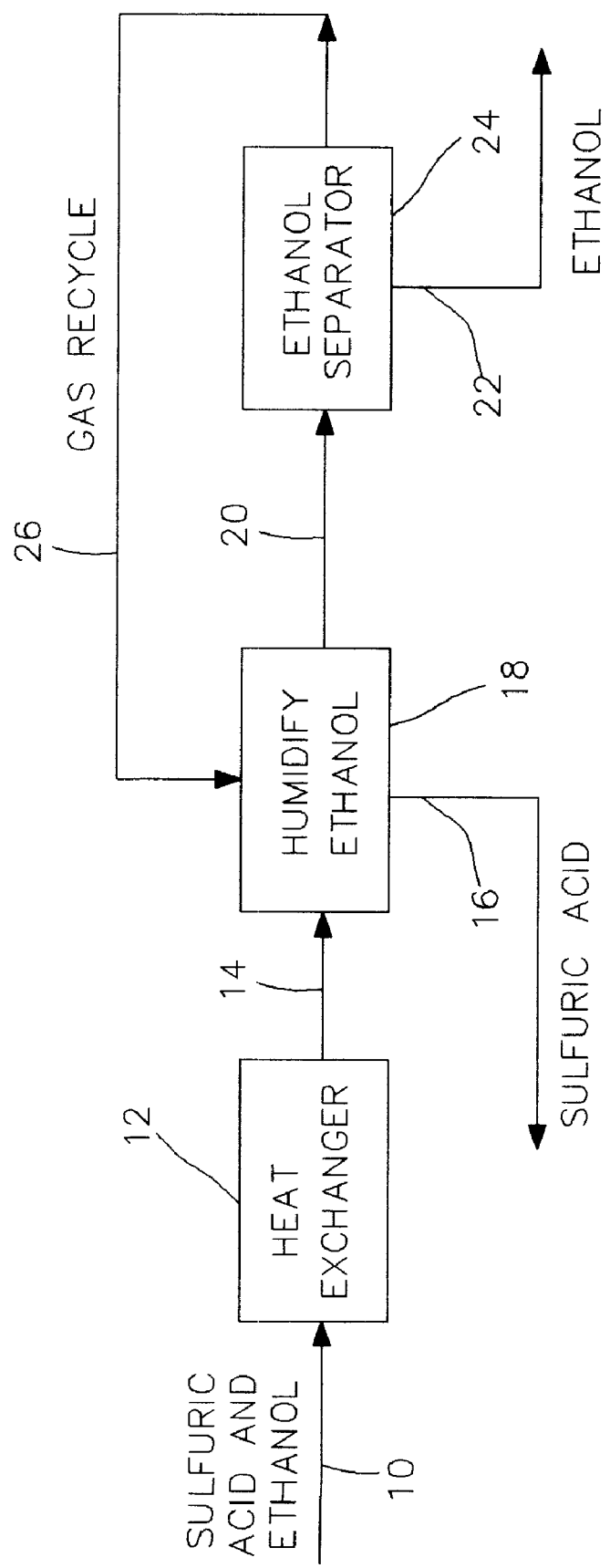
FIG. 1 is a flow sheet denoting the invention as set forth in the appended claims.

In the preferred embodiment of the present invention, a mixture of ethanol and sulfuric acid is conveyed to a vessel and a gas is added to the vessel, to be employed, to humidify ethanol contained in the mixture. The humidified gas is then removed from the vessel to produce sulfuric acid substantially free of ethanol. The operating temperature range is about 20° C. to about 80° C.

The flow diagram of FIG. 1 illustrates the general preferred embodiments of the present invention. In the diagram, rectangles represent stages or functions of the present invention and not necessarily separate components. Arrows indicate direction of flow of material in the method.

Referring to FIG. 1, a mixture of ethanol and sulfuric acid 10, is conveyed into a heat exchanger 12, where the heated mixture 14, is forwarded to a stage to humidify ethanol 18 by a recycle gas 26 to form a gas which is humidified with ethanol 20 and then conducted to an ethanol separator stage 24 to produce ethanol 22. The mixture 14, consequent to a substantial withdrawal of ethanol from the mixture, provides sulfuric acid 16. Recycle gas 26 is, to some extent, separated from the ethanol separator stage 24. The functions of heat exchange 12 and also to humidify ethanol 18 are often combined in a single stage. The stage to humidify ethanol 18 is frequently a vessel constructed of acid proof materials. Sulfuric acid 16 is customarily employed to depolymerized cellulose and depolymerized hemicellulose from a biomass material.

Referring to FIG. 2, a flow sheet denoting a preferred separating method for parting ethanol from a gas humidified with ethanol. A gas humidified with ethanol 20 is conveyed into a heat exchanger 28, where the cooled mixture 30, is conveyed to an ethanol condenser 34 to form ethanol 32 and an ethanol containing gas for recycle 36. The heat exchange stage 28 and an ethanol condenser stage 34 are often combined in a single stage.

Referring to FIG. 3, a flow sheet denoting an alternate method for separating ethanol from a gas humidified with ethanol. A gas humidified with ethanol 20 is conveyed into a gas compressor 38, where the gas is pressurized to form compressed gas 40, which is then conveyed to an ethanol condenser 44 to condense ethanol and form ethanol 42 and an ethanol containing gas for recycle 48. The gas compressor stage 36 and an ethanol condenser stage 44 are often combined in a single stage.

EXAMPLES

The following examples are set forth to illustrate more clearly the principles and practice of the invention. Where parts or quantities are mentioned, the parts or quantities are by volume.

Example 1

To prove the method, a synthetic mixture composed of 50 c.c.s of denatured alcohol and 50 c.c.s of concentrated sulfuric acid is combined in form a synthetic mixture. The concentrated sulfuric acid contains about 40% water to about 10% water. For availability and convenience, air is employed for humidification in the example. The synthetic mixture, contained in an eight ounce glass, is subjected to four hours of humidification of the synthetic mixture with air from an air pump. The eight ounce glass, and contents, are regulated in a water bath maintained at a temperature of about 55° C. The air containing humidified ethanol in air is discarded. The synthetic mixture, containing about 50 c.c.s, was inspected for alcohol aroma and found to be devoid of a scent of alcohol therefore removing alcohol from concentrated sulfuric acid.

Example 2

To create humidified ethanol in air, air is steadily conveyed and distributed in a glass container containing denatured alcohol at about 55° C., and forms humidified air saturated with ethanol. The humidified air is conveyed from the glass container. The conveyed humidified air is about 55° C. and is cooled to about 40° C. in a water cooled condenser. The cooled air then forms a condensate of liquid alcohol and creates humidified air saturated with ethanol at about 40° C. The air may be recovered and may be recycled for subsequent humidifcation of ethanol.

What is claimed is:

1. A method to separate ethanol from a solution containing ethanol and sulfuric acid which comprises:

supplying a solution containing ethanol and sulfuric acid;

supplying a gas to humidify said ethanol;

adding said solution and said gas within a vessel to form a gas humidified with ethanol;

withdrawing the gas humidified with ethanol from said vessel;

supplying heat to said solution to replace heat of vaporization of the humidified ethanol;

removing the sulfuric acid from said vessel whereby ethanol is separated from solution containing ethanol and sulfuric acid to obtain sulfuric acid substantially free of ethanol.

2. The method of claim 1 wherein the gas humidified with ethanol, withdrawn from said vessel, is cooled to condense ethanol to form ethanol as a liquid and the gas is recovered for recycle for subsequent humidification of ethanol.

3. The method of claim 1 wherein the gas humidified with ethanol, withdrawn from said vessel, is pressurized and then condensed to form ethanol as a liquid and the gas is recovered for recycle for subsequent humidification of ethanol..

4. The method of claim 1 wherein said vessel is of substantially of acid proof materials.

5. The method of claim 1 wherein the sulfuric acid, substantially free of ethanol, contains glucose and pentoses.

6. The method of claim 1 wherein said solution containing ethanol and sulfuric acid contains depolymerized cellulose and depolymerized hemicellulose.

7. The method of claim 1 wherein said sulfuric acid, substantially free of ethanol, is employed to depolymerized cellulose and depolymerized hemicellulose.

8. The method of claim 1 wherein said heat is waste heat energy.

9. The method of claim 1 wherein said heat is provided from a flue gas.

10. The method of claim 1 wherein said sulfuric acid contains about 40% water to about 10% water.

11. The method of claim 1 wherein said gas to humidify said ethanol is air.

* * * * *